United States Patent
Fleenor (12)

(10) Patent No.: US 6,221,084 B1
(45) Date of Patent: Apr. 24, 2001

(54) KNOT TYING APPARATUS HAVING A NOTCHED THREAD COVER AND METHOD FOR USING SAME

(75) Inventor: Richard P. Fleenor, Englewood, CO (US)

(73) Assignee: Parc Surgical, Inc., Englewood, CO (US)

( * ) Notice: Subject to any disclaimer, the term of this patent is extended or adjusted under 35 U.S.C. 154(b) by 0 days.

(21) Appl. No.: 09/232,393

(22) Filed: Jan. 15, 1999

(51) Int. Cl.⁷ .................................................. A61B 17/00
(52) U.S. Cl. .................................................. 606/148
(58) Field of Search .................................. 606/148, 144, 606/139, 145, 150, 151, 158, 205, 206, 208, 167, 170, 171; 112/169, 80.03; 289/17; 604/104–106

(56) References Cited

U.S. PATENT DOCUMENTS

| | | |
|---|---|---|
| 2,137,710 | 11/1938 | Anderson . |
| 2,316,297 | 4/1943 | Southerland et al. . |
| 2,455,833 | 12/1948 | Trombetta . |
| 3,985,138 | 10/1976 | Jarvik . |
| 3,995,619 | 12/1976 | Glatzer . |
| 4,038,988 | 8/1977 | Perisse . |
| 4,050,465 | 9/1977 | Perisse . |
| 5,112,299 | 5/1992 | Pascaloff . |
| 5,144,961 | 9/1992 | Chen et al. . |
| 5,196,022 | 3/1993 | Bilweis . |
| 5,211,650 | 5/1993 | Noda . |
| 5,284,485 | 2/1994 | Kammerer et al. . |
| 5,308,357 | 5/1994 | Lichtman . |
| 5,312,423 | 5/1994 | Rosenbluth et al. . |
| 5,318,578 | 6/1994 | Hasson . |
| 5,320,630 | 6/1994 | Ahmed . |
| 5,397,326 | 3/1995 | Mangum . |
| 5,423,837 | 6/1995 | Mericle et al. . |
| 5,454,820 | 10/1995 | Kammerer et al. . |
| 5,454,821 | 10/1995 | Harm et al. . |
| 5,472,446 | 12/1995 | de la Torre . |
| 5,527,323 | 6/1996 | Jervis et al. . |
| 5,549,618 | 8/1996 | Fleenor et al. . |
| 5,741,280 | 4/1998 | Fleenor et al. . |
| 5,810,845 | * 9/1998 | Yoon .................................. 606/139 |

FOREIGN PATENT DOCUMENTS

| | | |
|---|---|---|
| 0634143A2 | 1/1995 | (EP) . |
| 2127844 | 1/1995 | (CA) . |
| 95/19139 | 7/1995 | (WO) . |
| 97/17901 | 5/1997 | (WO) . |
| 98/11825 | 3/1998 | (WO) . |

* cited by examiner

Primary Examiner—Henry J. Recla
Assistant Examiner—Vikki Hoa Trinh
(74) Attorney, Agent, or Firm—Gibson, Dunn & Crutcher LLP

(57) ABSTRACT

The present invention provides a knot tying apparatus having a notched thread cover and methods for using such a knot tying apparatus for placing knots. The present invention has particular utility in tying and placing knots during laparoscopic surgery. The thread cover includes at least one notch in the distal end which is sized so as to allow a thread such as a suture thread to pass therethrough while preventing a knot in the thread from passing therethrough. Using the notched thread cover which is attached to the distal end of a knot tying apparatus, it is possible to both pull and push on the knot when cinching the knot around the member being tied. Being able to simultaneously push and pull on the knot minimizes the forces exerted against the member being tied, thereby reducing the likelihood that fragile members such as blood vessels and the like are damaged during the tying procedure. The knot tying apparatus includes a knot carrier and a knot slider slidably connected thereto. The thread cover preferably at least partially surrounds a knot carrier and is connected to the distal end of a knot slider.

36 Claims, 4 Drawing Sheets

KNOT TYING APPARATUS HAVING A NOTCHED THREAD COVER AND METHOD FOR USING SAME

FIELD OF THE INVENTION

The present invention relates to the broad field of knot tying, and particularly knot tying in the context of medicine such as the tying of sutures. The invention has special applicability to the placement and tying of sutures and other knots in the field of laparoscopic surgery. More particularly, the present invention relates to a knot tying apparatus which enables knots to be cinched while reducing the pulling forces against the member to which the knot is applied, thereby minimizing the trauma to the member being tied.

BACKGROUND OF THE INVENTION

Knot tying and suturing as a method to approximate tissue is a critical element of surgery. Skill in knot tying is so basic to surgery that medical students learn knot tying early in their studies, and they routinely practice tying various kinds of knots with one or both hands.

In laparoscopic procedures, the tying of sutures and other knots is especially difficult and it is not uncommon for the tying of a single knot to require an hour or more. In laparoscopy, there is no tactile sense to the surgeon because of the surgeon's lack of direct contact with the tissue, since the surgeon's sense of feel is reduced by the imposition of the laparoscopic instruments. Further, the surgeon is unable to view directly the site of the surgery, but instead must rely upon a two-dimensional video screen which both magnifies the site and eliminates the opportunity for any depth perception.

Another difficulty is presented by the fact that laparoscopic surgery necessarily is conducted in a confined space, and the instruments are preferably positioned in this confined space in a particular orientation in relation to one another and in relation to the patient. For example, it is desirable that within this confined space, the instruments not be too close together or too far apart, that they be visible through the laparoscope, and that they enter the field of view of the laparoscope tangentially rather than coaxially so that they do not unduly obstruct the surgeon's view. It is also desirable that the instruments advance out of their sheaths toward the video screen and away from the laparoscope in order to avoid the surgeon having to operate under "mirror vision." Finally, procedures employing a single operating port encourage the surgeon to use the dominant hand to manipulate the instrument in the port while using the other hand merely to stabilize the laparoscopic sheath. However, knot tying typically requires both hands, and so an assistant or a device is then necessary to stabilize the sheath while both the surgeon's hands tie the knot.

Suturing and other knot tying are applicable to many different laparoscopic procedures. In laparoscopic cholecystectomy, the cystic duct or artery can be ligated using manual suturing or knot tying techniques rather than an automatic clip. In a laparoscopic appendectomy, the surgeon can use slip knots rather than using a disposable linear stapler. Although laparoscopic staplers have been developed, laparoscopic sutures and other knots will still be needed for many purposes such as closing defects in a staple line, placing purse-string sutures for end-to-end stapling, closing mesenteric defects, and ligating large blood vessels.

Knots used in laparoscopy may be tied either intracorporeally or extracorporeally. Internal knotting requires a high level of expertise by the surgeon, and normally requires at least two operating cannulae and associated graspers. For a square knot, a loop is made in a first end of the material using the first grasper; the second grasper is inserted through the loop and used to grasp the second end; the second end is pulled through the loop to produce a flat knot; another loop is made in the first end of the material using the first grasper; the second grasper is inserted through that loop and used to grasp the second end; and the second end is pulled through that loop to produce an opposing flat knot. The resulting square knot can then be tightened with the two graspers. The first throw may be a simple overhead knot or may be a surgeon's knot. Additional throws may be applied over the second throw to provide additional security. It is important that sequential throws are in opposite directions to avoid producing a "granny" knot.

Many other types of knots are possible depending on the characteristics of the material used, the dexterity of the surgeon, and the circumstances at the suture site. Many knots in laparoscopy are slip knots of some kind to allow the knot to be cinched against the sutured material. These include the Roeder knot, a cinch knot, and so-called "hangman's" knots.

Extracorporeally tied knots are obviously much easier to tie than intracorporeally tied knots, but extracorporeally tied knots can be very difficult to place effectively. A number of devices have been developed to assist in placing an extracorporeally tied knot including the "Clarke" ligator, the "Weston" ligator (see "A New Cinch Knot", *Obstetrics & Gynecology*, Vol. 78, No. 1, July 1991, 144–47) and other devices. See, e.g., "An Improved Needleholder for Endoscopic Knot Tying", *Fertility and Sterility*, Vol. 58, No. 3, Sept. 1992, 640–42; "Roeder Knot for Tight Corners in Conventional Abdominal Surgery", J. R. Coll. Surg. Vol. 36, Dec. 1991, 412; "A Simple Method for Ligating with Straight and Curved Needles in Operative Laparoscopy", *Obstetrics and Gynecology*, Vol. 79, No. 1, Jn. 1992, 143–47. Most of the devices for placing an extracorporeally tied knot fall into the category of "knot pushers." A knot is formed extracorporeally and is pushed through the cannula by sliding it down the material using a device that engages the knot. The Clarke ligator mentioned above was one of the first knot pushers. It simply consists of a grasping end and an end opposite the grasping end with an open ring. It engages the knot by passing the material through the opening in the ring.

There are also a number of patented knot pushers, including those described in U.S. Pat. No. 5,234,445 by Walker, U.S. Pat. No. 5,234,444 by Christondias, U.S. Pat. No. 5,217,471 by Burkhart, U.S. Pat. No. 5,192,287 by Fournier, U.S. Pat. No. 5,163,946 by Li, U.S. Pat. No. 5,129,912 by Noda, U.S. Pat. No. 5,133,723 by Li, U.S. Pat. No. 5,084,058 by Li, U.S. Pat. No. 3,871,379 by Clarke, and U.S. Pat. No. 2,012,776 by Roeder. There are also a number of patents directed more towards endoscopic knotters, including U.S. Pat. No. 5,234,443 by Phan, U.S. Pat. No. 5,211,650 by Noda, U.S. Pat. No. 4,961,741 by Hayhurst, U.S. Pat. No. 4,923,461 by Caspari, U.S. Pat. No. 4,890,614 by Caspari, U.S. Pat. No. 4,641,652 by Hatterer, and U.S. Pat. No. 4,602,635 by Mulhollan.

A problem with many existing knot tying apparatus is that the knot is tied and cinched by pulling the knot tying apparatus away from the member being sutured. This pulling or tugging action can damage or traumatize the member being tied or sutured. It also creates the risk of pulling a suture out of the tissue which has been stitched. Thus, there remains a need for a knot tying apparatus designed so as to minimize or eliminate the forces generated against the member being sutured during the tying and cinching process.

SUMMARY OF THE INVENTION

The present invention satisfies the need identified above by providing a knot tying apparatus and methods for its use in which the pulling motion used to form and tighten a knot are counterbalanced by a pushing motion in which an at least partially formed knot is slid along the thread attached to the member being tied by a specially designed thread cover attached to the distal end of the knot tying apparatus. The present invention is especially useful for, but not limited to, placing a pre-tied extracorporeal knot, with particular but not exclusive application to laparoscopy. The knot may be a slip knot or some other knot, especially a knot that can be formed by passing the free end through a knot body which includes a loop or set of loops.

The knot tying apparatus of the present invention includes a thread cover located at the distal end of the apparatus which generally comprises a sheath having an inner cavity, a proximal end, and a distal end, the inner cavity being sized and shaped to accommodate a thread disposed therein. The thread cover also includes at least one notch in the distal end of the sheath. The width of the notch or notches is sufficient to allow thread such as suture thread to slide therethrough. However, the notch is not wide enough to allow a knot or partially formed knot in the thread to pass therethrough. Thus, after a thread is placed adjacent a member to which the knot is to be applied (for example, a section of tissue or a vessel to being sutured) using the knot tying apparatus to discharge and place the necessary thread and the at least partially tied knot, the notch in the thread cover is used to engage and hold the knot or partially formed knot against the exterior surface of the sheath of the thread cover. The thread cover can then be used to slide the at least partially formed knot along the thread toward the member to which the knot is to be applied. Thus, unlike other knot tying apparatus in which the knot tying apparatus only tightens and cinches the knot by pulling on the thread which encircles or passes through the member being tied, the knot tying apparatus of the present invention allows the user to independently or simultaneously push the knot toward the member being sutured. By simultaneously exerting a pulling and pushing motion to tighten the knot, a tighter and superior knot can be formed and the risk of damage or trauma to the member which can occur if only a tugging force is exerted can be significantly reduced In one embodiment, the sheath of the thread cover is adapted at its proximal end to be connected to a knot slider which displaces thread into the cavity of the thread cover and ultimately outside the thread cover so that the thread can be positioned around the member to be sutured. Preferably, the sheath of the thread cover contains an aperture or slot near its proximal end into which a protrusion on the knot slider fits. This holds the thread cover in a firm and fixed orientation with respect to the longitudinal axis of the knot slider.

The number of notches or slots in the thread cover can vary. A plurality of notches can be beneficial in allowing the user to engage the knot or partially formed knot in the notch of the thread cover without having to twist the knot tying apparatus to align the notch and knot. In a preferred embodiment, the thread cover is substantially cylindrical and two notches are positioned approximately 180 degrees apart.

The knot tying apparatus of the present invention is similar to that described in U.S. Pat. No. 5,741,280 to Fleenor and assigned to the assignee of the present invention, this patent being incorporated herein by reference. In general, the overall knot tying device includes a knot pusher assembly that comprises a knot carrier tube with three concentric ferrules, the most distal of which is the thread cover of the present invention. One of these ferrules (referred to as the mating ferrule or knot carrier) is threaded or otherwise removably attached to one of the ends of the knot carrier tube so that the ferrule and the tube share one flush end and the knot carrier tube extends beyond the ferrule and extracorporeally at the other end. A second ferrule (also referred to herein as the proximal ferrule or knot slider) is slidably attached concentrically over the first ferrule. A protrusion on the first ferrule limits the range of motion of the second ferrule. The second ferrule is not as long as the first ferrule so that the first ferrule extends beyond both ends of the second ferrule regardless of the sliding of the second ferrule.

The third ferrule is a thread cover. It is located concentrically around the first ferrule and is attached to the second ferrule. The thread cover is radially spaced apart from the first ferrule to define an annular space there between. The thread cover is attached to the second ferrule so that they slide together.

The knot material including a knot or a partially formed knot is wound around the first ferrule in the annular space defined between the first ferrule and the thread cover. One end of the knot material is attached to the second ferrule. The other end of the knot material extends off of the flush edge of the first ferrule and the knot carrier tube and terminates at a needle.

A knot release tube is placed concentrically around a segment of the knot carrier tube. One edge of the knot release tube abuts against the edge of the second ferrule opposite the edge of the second ferrule that connects to the thread cover. The knot release tube extends towards the end of the knot carrier tube opposite the end to which the first ferrule attaches, but does not reach that end so that the knot carrier tube protrudes beyond the knot release tube. The purpose of the knot release tube is to allow the second ferrule to be slid over the first ferrule in the direction of the flush end of the first ferrule and the knot carrier tube. This occurs when the end portion of the knot carrier tube without the first ferrule is held fixed and the knot release tube is pushed in the direction of the second ferrule.

The knot and knot material are deployed by the sliding of the second ferrule towards the flush end of the first ferrule and the carrier tube after the needle has been passed around an object to be tied (or some other knot need is met) and then passed into the device in the space bounded by the ferrules. The annular ridge of the second ferrule pushes the windings of the knot material off of the first ferrule. The windings are wound around the mating ferrule to form an at least partially formed knot, and when a sufficient number of windings are pushed off of the first ferrule the free ends of the knot material may be tensioned to form a complete knotted loop.

It is an object of the invention to provide a disposable cartridge that contains the knot material and knot so that multiple knots may be quickly, easily, and inexpensively placed. In an embodiment of the present invention, the three ferrules, knot material, and knot may be inexpensively manufactured in bulk. The three ferrules are made of molded plastic. The second ferrule is placed around the first ferrule and the knot material, such as standard suture material, is wound over the first and second ferrules as described above. The third ferrule or thread cover is then placed over the windings and attached to the second ferrule and the cartridge is complete. After a completed knot has been separated from the ferrules, the spent cartridge may simply be removed from the knot carrier tube and a new cartridge may be reloaded onto the knot pusher to place another knot.

The method of the present invention generally involves initially positioning the knot tying apparatus just described near a member to be tied or sutured. A knot or partially formed knot is then placed near the member using the knot tying apparatus to discharge the necessary thread. The thread cover of the present invention is then utilized to engage the at least partially formed knot. As noted earlier, the at least partially formed knot can be held in abutting relationship against the exterior of the thread cover because the notch or notches in the thread cover are large enough to permit thread such as suture thread to pass therethrough but not wide enough to allow a knot or partially formed knot from passing therethrough. Once the knot or partially formed knot is positioned at a notch, the knot is slid along the thread surrounding or passing through the member being tied or sutured by pushing the knot along a portion of the thread with the thread cover; typically, the knot is pushed toward the member being tied.

Preferably, the knot is also tightened or cinched by using the knot tying apparatus to pull on the thread, the pulling action being away from the member being sutured. Most preferably, one end of the thread which forms the knot is pulled on by the knot tying apparatus while the knot is simultaneously pushed towards the member using the notched thread cover. As noted above, the pushing motion achieved with the thread cover counteracts the tugging motion and lessens the possibility of damaging the member while tightening or cinching the knot. This is of particular value in the field of laparoscopic surgery given the fragility of many of the members to which knots are tied (for example, blood vessels and veins, various tissues, etc.).

In one embodiment, knot tying apparatus includes a jaws for pulling on one end of the thread of which the knot is made. Preferably, the jaws are capable of being withdrawn so as to be at least partially surrounded by the thread cover.

Although the system is described principally in the preferred embodiment of laparoscopy applications, it can be appreciated that the system is also suitable for many other intracorporeal and extracorporeal applications.

DETAILED DESCRIPTION OF THE INVENTION

The present invention provides an improved knot tying apparatus and methods for its use in tying knots. The knot tying apparatus of the present invention includes a thread cover which allows knots to be tightened and cinched not only by pulling on the thread or knot material which makes up the knot, but also by pushing the knot toward the member around or through which the knot is attached. The pulling or tugging motion typically employed with a knot tying apparatus to tighten a knot also pulls or tugs on the member being tied, thus creating the possibility that the member may be damaged and/or the knot material pulled from the member being tied or sutured.

Using the knot tying apparatus of the present invention with its notched thread cover, the normal tugging action can be counterbalanced by a pushing motion as the knot or partially formed knot is engaged by a notch in the thread cover and then slid along a portion of the thread using the thread cover, generally in the direction toward the member being tied. Thus, using a knot tying apparatus of the present invention it is possible to significantly lessen the potential for traumatizing or damaging the member to which the knot is tied. Being able to both simultaneously pull and push on the knot in tightening and cinching the knot also yields a better formed and tighter knot. Furthermore, unlike many existing knot tying apparatus, the apparatus of the present invention allows the user such as a surgeon to pull up on a portion of the apparatus which can be used to grasp the thread while maintaining a tactile feel for how tight the knot or suture is being pulled around the object being tied (e.g., a tissue).

Figure 5E:
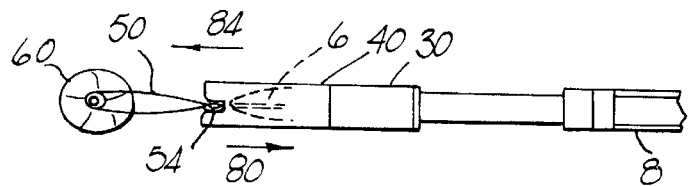
FIG. 5E shows a perspective view of a released knot being tightened by pulling on the knot and using the thread cover of the present invention to push the knot along a portion of thread.
Figure 6B:
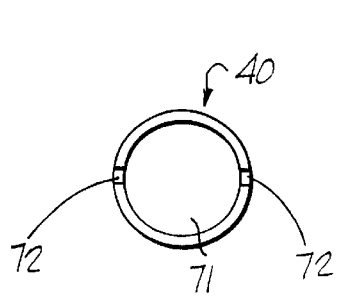
FIG. 6B is an end view of the thread cover of the present invention.
Figure 6A:
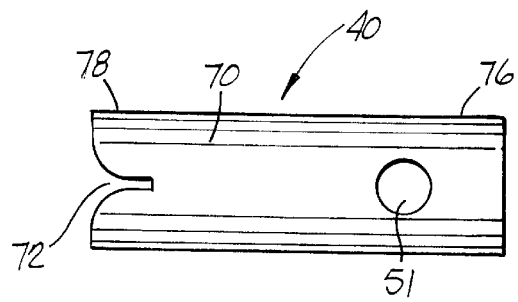
FIG. 6A is a side elevation of the thread cover of the present invention.
Figure 6C:
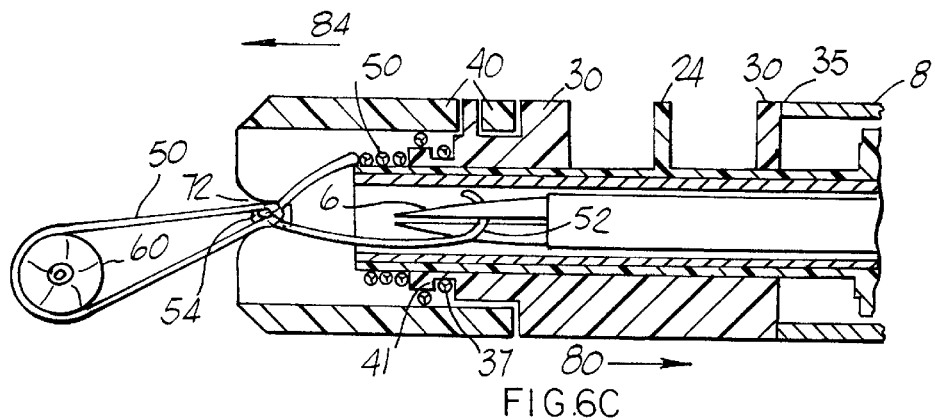
FIG. 6C is a detailed side-sectional view of the knot deployment end of the knot tying apparatus showing the knot engaged with the notch in the thread cover of the present invention and the pulling and pushing forces exerted to tighten the knot.

The thread cover 40 utilized in the knot tying apparatus of the present invention is illustrated most clearly in FIGS. 6A and 6B and comprises a sheath 70 which surrounds an inner cavity 71, the sheath having a proximal end 76 and a distal end 78. The inner cavity 71 is sized and shaped to accommodate a thread or knot material 50 disposed therein and also is preferably large enough to at least partially accommodate a portion of a knot slider which discharges thread into the thread cover cavity. At least one notch 72 is located at the distal end 78 of the sheath 70. The width of the notch 72 is carefully sized so that the notch 72 is sufficiently wide so as to allow a portion of thread or knot material 50 to slide through the notch 72. However, the notch 72 is designed to be too narrow to allow a knot 54 or partially formed knot in the thread 50 to slide through the notch 72. Thus, as shown in FIGS. 5E and 6C, it is possible to engage a knot 54 or partially formed knot against the exterior of the sheath 70 and slide the knot (in the direction designated by reference arrow 84) toward the member 60 to which the knot is being applied. The actual thickness of the notch 72 of course can be varied according to the thickness of the particular thread 50 being used; the key requirement is that the notch 72 be sufficiently narrow that a knot 54 or partially formed knot in the thread 50 can not pass through the notch 72.

Figure 2:
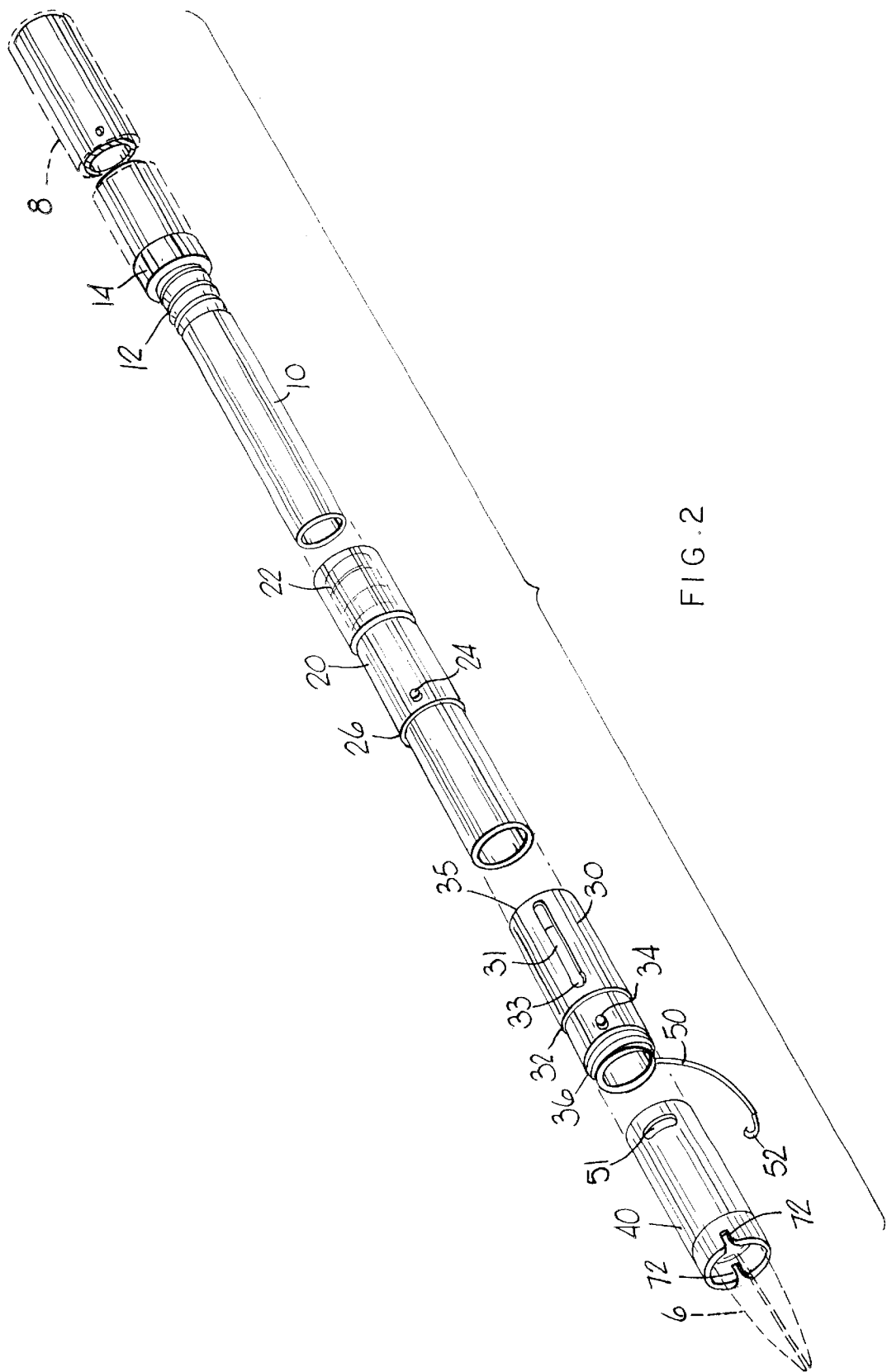
FIG. 2 shows an exploded view of the components of the apparatus of FIG. 1.

The thread cover 40 must have at least one notch 72 and may include a plurality of notches. In a preferred embodiment such as illustrated in FIGS. 2 and 6B, the sheath 70 is substantially cylindrical and includes two notches 72 which are approximately on opposite sides of the sheath 70, i.e., approximately 180 degrees apart. There may be an advantage to having multiple notches in that such a design allows the knot to be engaged with only a minimal rotation of the knot tying apparatus to align the notch with the knot. As described in greater detail below, the sheath 70 includes a means for connecting the thread cover at the distal end of the knot tying apparatus. In preferred embodiment, an aperture or hole 51 in the sheath 70 engages a protrusion on the knot tying apparatus to hold the thread cover 40 at the distal end of the knot tying apparatus.

Figure 1:
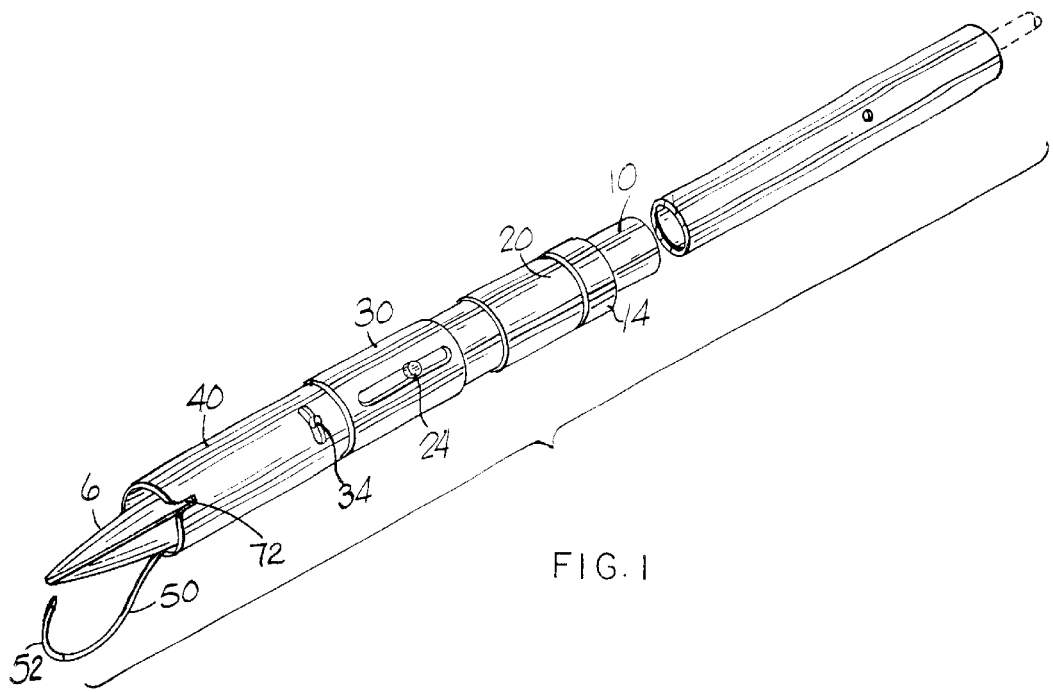
FIG. 1 shows a perspective view of an apparatus in accordance with the present invention.
Figure 3:
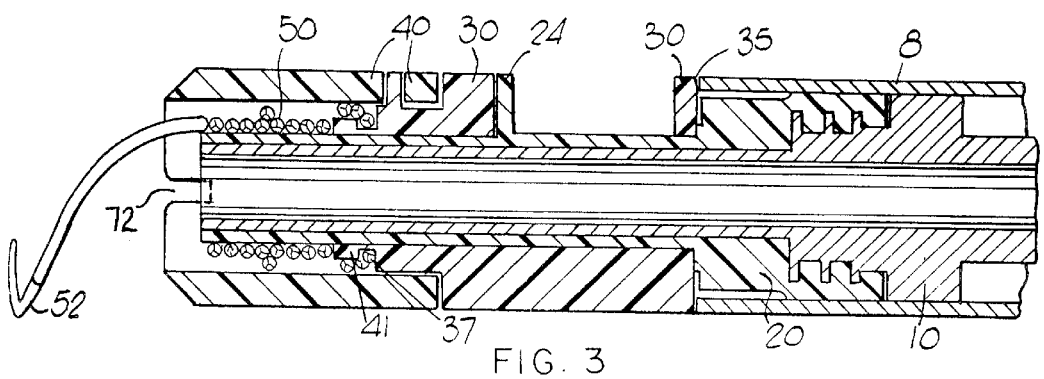
FIG. 3 shows a detailed side-sectional view of the knot deployment end of the apparatus depicted in FIG. 1 before the knot material has been released.
Figure 4:
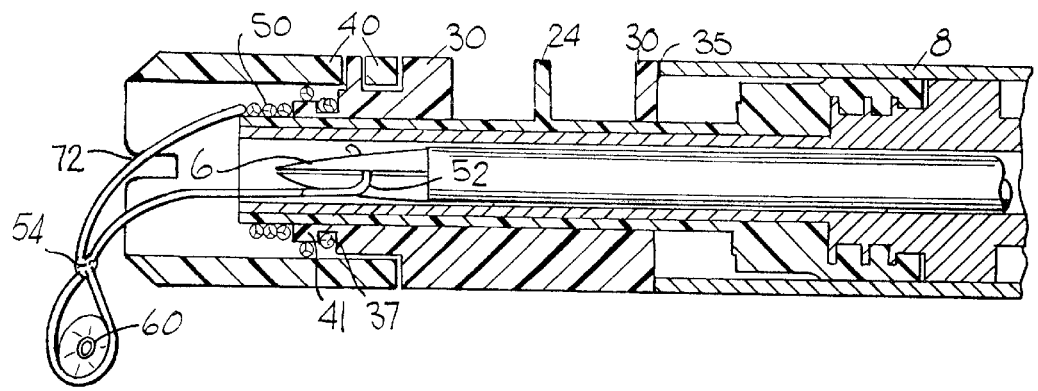
FIG. 4 shows the view of FIG. 3 after the knot material has been partially released.

A perspective view of a portion of a preferred embodiment of the invention in which the thread cover 40 is attached to the other components of a knot tying apparatus is shown in FIG. 1. The knot tying apparatus includes a knot carrier tube 10, a mating ferrule 20 (also referred to as the knot carrier), a proximal ferrule 30 (also referred to as a knot slider), a distal ferrule or thread cover 40, thread or knot material 50, needle 52, and knot material clenching jaws 6. An exploded view of these components is shown in FIG. 2, and detailed side-sectional views are shown in FIGS. 3 and 4. The mating ferrule 20, proximal ferrule 30, and thread cover 40 are all coaxial with the knot carrier tube 10. In a preferred embodiment of the invention, the mating ferrule 20 fits around the knot carrier tube 10 so that one end of the mating ferrule 20 is flush with an end of the tube 10 and that threads 22 on the inside of the other end of the mating ferrule 20 mate with threads 12 on the outside of the knot carrier tube 10. The knot carrier tube 10 extends beyond the threaded end of the mating ferrule 20.

In this description of an embodiment of the invention, the direction towards the flush end of the knot carrier tube 10 and the mating ferrule 20 is termed the "distal" direction and the direction towards the opposite end of the knot carrier tube 10 and the mating ferrule 20 is termed the "proximal" direction. The distal direction may extend beyond the flush ends of the knot carrier tube 10 and the mating ferrule 20 and the proximal direction may extend beyond the opposite end of the knot carrier tube 10. "Longitudinal" and "tangential" as used herein are with respect to the axis of the knot carrier tube 10.

An annular ridge 14 is located on the knot carrier tube 10 immediately proximal to the knot carrier tube 10 threads 12 so that the mating ferrule 20 will abut against the ridge 14 when the mating ferrule 20 is completely threaded around the knot carrier tube 10. At that point, no further rotation of the mating ferrule 20 is possible.

The proximal ferrule 30 is slidably located around the mating ferrule 20. A protrusion 24 on the mating ferrule 20 extends through a slot 31 in the proximal ferrule 30 so that the proximal ferrule 30 may be slid longitudinally over the mating ferrule 20 for the length of the slot 31. When the proximal ferrule 30 is positioned as far to the proximal end as possible (i.e., when the protrusion 24 contacts the distal end of the slot 31), the proximal ferrule 30 abuts against an annular edge 26 of the mating ferrule 20. The slot 31 has an irregularity 33 at its distal end so that the protrusion 24 will achieve an interference fit in the irregularity 33. The initial position of the proximal ferrule 30 is with the protrusion 24 fit into the irregularity 33.

The thread cover 40 is located partially around the proximal ferrule 30 and is attached thereto so that sliding the proximal ferrule 30 also slides the thread cover 40. The thread cover 40 abuts against an annular edge 32 located on the proximal ferrule 30. The annular edge 32 is located distal to the slot 31 on the proximal ferrule 30. The distal end of the thread cover 40 extends beyond the distal end of the proximal ferrule 30 and concentrically around the mating ferrule 20 to define an annular space between the mating ferrule 20 and the thread cover 40. The thread cover 40 is attached to the proximal ferrule 30 by the extension of a protrusion 34 located on the proximal ferrule 30 through a slot 51 located on the thread cover 40. The slot 51 is only as wide as the protrusion 34 so that the thread cover 40 is fixed with respect to the proximal ferrule 30 in the longitudinal direction.

The knot material 50 is wound around the distal portion of the proximal ferrule 30 with windings extending beyond the distal edge of the proximal ferrule 30 and onto the mating ferrule 20. With reference to FIG. 3, the placement of the windings relative to the mating ferrule 20, proximal ferrule 30, and thread cover 40 may be understood. FIG. 3 depicts the knot material 50 when the proximal ferrule 30 is placed in its initial position. The windings of the knot material 50 begin in an annular notch 37 formed in the distal end of the proximal ferrule 30 where a portion of the thread containing one end of the thread is placed. While two windings are shown in the notch 37 in FIG. 3, the notch 37 may be dimensioned to hold any number of windings. The windings of the knot material 50 pass from the notch 37 over an annular ridge 41 in the proximal ferrule 30 and continue around the mating ferrule 20 in the annular space between the mating ferrule 20 and the thread cover 40. The windings pass over the distal edge of the mating ferrule 20 and continue so that a strand of knot material 50 extends beyond the edge the mating ferrule 20 and hangs free from the ferrules and the knot carrier tube 10. The other end of the knot material 50 terminates at needle 52. The knot material 50 is wound around the mating ferrule 20 so that a desired partially formed knot will result when a sufficient number of windings of the knot material 50 have been pushed off of the mating ferrule 20.

A knot release tube 8 is placed concentrically around a segment of the knot carrier tube 10, as shown in FIGS. 2, 3 and 4. One edge of the knot release tube 8 abuts against the edge 35 of the proximal ferrule 30 opposite the edge of the proximal ferrule 30 that connects to the thread cover 40. The knot release tube 8 extends towards the proximal end of the knot carrier tube 10, but does not reach that end so that the knot carrier tube 10 protrudes beyond the knot release tube 8. The purpose of the knot release tube 8 is to allow the proximal ferrule 30 to be slid over the mating ferrule 20 in the distal direction. This occurs when the proximal end of the knot carrier tube 10 is held fixed and the knot release tube 8 is pushed in the distal direction. Thus, the proximal ferrule 30 can be moved by manipulating the proximal ends of the knot release tube 8 and the knot carrier tube 10.

It is a primary object of the present invention to allow a knot to be placed near its desired final position before releasing the knot material 50 from the mating ferrule 20 by positioning the knot carrier tube 10 in close proximity to the desired final position of the knot. Afterwards, the needle 52 is passed around the feature or member to be tied and then placed into the region partially enclosed by the tube 10 and the ferrules. Next, the knot material 50 is released from the mating ferrule 20, and the free ends of the knot material 50 are tensioned to form a completed knot around a feature.

With reference to FIG. 4, the deployment of the knot material 50 away from the mating ferrule 20 may be understood. By manipulating the knot release tube 8 and the knot carrier tube 10, the proximal ferrule 30 is slid in the distal direction. As discussed above, sliding the proximal ferrule 30 also slides the attached thread cover 40. As the annular ridge 41 on the proximal ferrule 30 moves in the distal direction, it forces the knot material 50 towards the distal end of the mating ferrule 20. The windings of the knot material 50 fall off of the edge of the mating ferrule 20 as the ridge 41 moves in the distal direction. As the windings fall off of the edge of the mating ferrule 20 they are no longer bounded by the mating ferrule 20. The knot material 50 is then available distal to the knot carrier tube 10 and may be manipulated by the clenching jaws 6.

The purpose of the annular notch 37 is to anchor an end of the knot material 50. One end of the knot material 50 is tied or otherwise attached to the annular notch 37. If the notch 37 and ridge 41 were not present, tension on the knot material 50 that is exterior to the mating ferrule 20 could pull all of the knot material 50 off of the mating ferrule 20 and the proximal ferrule 30. With the presence of the ridge 41, however, tension on the knot material 50 will pull the strands of the knot material 50 located in the notch 37 into the ridge 41 so that the knot material 50 will remain attached to the proximal ferrule 30.

Note that the ridge 41 does not completely enclose the knot material 50. The ridge 41 does not extend in the radial direction completely to the thread cover 40, because knot material 50 must be allowed to pass across the ridge 41. The strand or strands of knot material 50 that wrap around the notch 37 in the proximal ferrule 30 must be sufficiently tensioned so that the strand or strands wrapped around the notch 37 will not pass over the ridge 41. The initial tension on the windings of knot material 50 around the mating ferrule 20 is sufficient to prevent the knot material 50 from sagging away from the mating ferrule 20 but is not so great as to hinder the sliding of the knot material 50 off the mating ferrule 20 when the proximal ferrule 30 is slid. The tension of the winding material 50 may be controlled by, for instance, a cinch knot located in the notch 37 in the proximal ferrule 30.

In addition to serving as a means for sliding the knot 54 toward the member being tied as described above, the thread cover 40 serves several additional functions. It protects the knot material 50 from contamination and from becoming tangled on foreign objects before the knot material 50 is deployed. During the knot deployment process, the thread cover 40 aids the sliding of the knot material 50 off of the mating ferrule 20 by limiting the amount of potential overlap of the windings of the knot material 50 and preventing the windings from piling over each other. Because the windings are wound so as to form a particular partial knot, it is important that they are pushed off of the mating ferrule 20 in the correct order.

The annular edge 32 of the proximal ferrule 30 that abuts the thread cover 40 facilitates the sliding of the thread cover 40. Longitudinal force on the proximal ferrule 30 will be transmitted to the thread cover 40 over the entire surface of the annular edge 32 instead of merely at the slot 51 and the slot protrusion 34. Also, the longitudinal force on the proximal ferrule 30 is applied evenly around the circumference of the thread cover 40 instead of only at the location of the slot 51.

Figure 5A:
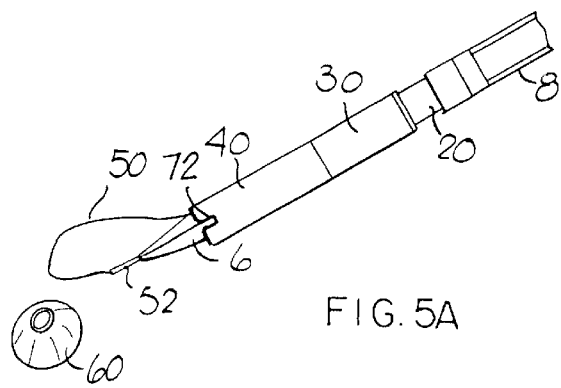
FIGS. 5A, 5B, and 5C, show a perspective view of a released knot being finished.
Figure 5B:
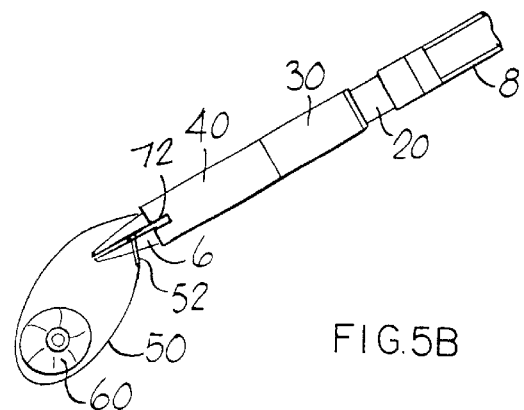
Figure 5C:
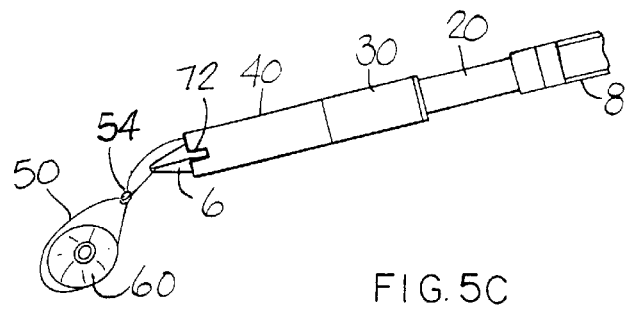
Figure 5D:
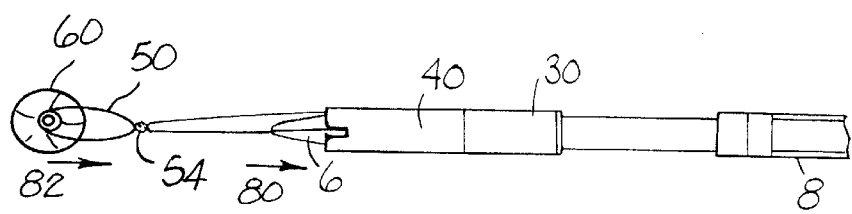
FIG. 5D shows a perspective view of a released knot being cinched by pulling on the knot tying apparatus.

With reference to FIGS. 5A through 5E, the method of using the knot tying apparatus of the present invention can be seen. As shown in FIG. 5A the needle 52 is placed in the clenching jaws 6 and the knot carrier tube 10 is positioned in the vicinity of the object or member 60 such as a vessel to be tied. As shown in FIG. 5B, an at least partially formed knot is then placed adjacent the member 60 to be tied. This may be accomplished by removing the needle 52 from the clenching jaws 6 and passing it through or around member 60 and then returning the needle to the clenching jaws 6 (such as by use of an additional grasper). The needle 52 is then pulled inside the distal end of the knot carrier tube 10 to allow the windings of knot material 50 in which a partial knot 54 is formed to be draped distal to the needle 52 and over a portion of the knot material 50 attached to the needle 52. As shown in FIG. 5C, the knot material 50 is released from the carrier tube 10 by pushing the release tube 8 while holding the carrier tube 10 fixed, which causes the ridge 41 of the proximal ferrule 30 to slide the knot material 52 off of the mating ferrule 20. The releasing of the knot material 50 allows the knot 54 to lightly cinch down on the lead end of the material which is grasped by the clenching the jaws 6.

As shown in FIG. 5D, the leads of the knot 54 are tensioned to firmly tie the member 60. With existing knot tying apparatus, tightening the knot 54 is typically accomplished by using the knot tying apparatus to pull on one end of the thread 50 in the direction indicated by reference arrow 80. The problem with tightening the knot in this manner is that the pulling motion also generates a pulling motion against the member 60 to which the knot is applied, as indicated by reference arrow 82. For delicate members such as blood vessels and the like, this tugging motion can damage the member 60 being tied. The tugging motion can also cause sutures to tear free.

In contrast, with the knot tying apparatus of the present invention, the knot 54 can be tightened by both a pulling and pushing action. The application of these countervailing forces minimizes the forces acting on the member 60 being tied, thereby significantly lessening the likelihood of injury to the member 60 during the tightening process. The present approach also yields a tighter and better formed knot.

As illustrated in FIGS. 5E and 6C, the pulling action can be accomplished using the knot tying apparatus of the present invention by moving the jaws 6 in the proximal direction (as indicated by reference arrow 80), while keeping the knot carrier tube 10 fixed. The knot 54 can also be tightened using the notch 72 located at the distal end 78 of the thread cover 40 to engage the knot 54 or partially formed knot. Once the knot 54 is engaged, the knot 54 or partially formed knot can be slid along a portion of the thread 50 using the thread cover 40 to push the knot 54 along the thread 50. The pushing action as indicated by reference arrow 84 is toward the member 60 to which the knot 54 is applied. Because the pushing force 84 largely opposes the pulling force 80, minimal net force is exerted against member 60, assuming the pulling and pushing motions are performed simultaneously, which is preferably the case. Once the thread 50 is sufficiently tightened around member 60, the leads of the knot material 50 may then be cut, either immediately adjacent to the knot or away from the knot to leave longer loose ends as desired.

In a preferred embodiment of the invention, the mating ferrule 20, proximal ferrule 30, thread cover 40, and knot material 50 are assembled in bulk and serve as a disposable knot carrying cartridge. The mating ferrule 20, proximal ferrule 30, and thread cover 40 are made of molded plastic. The knot carrying material 50 is standard medical suture material. The proximal ferrule 30 is placed over the mating ferrule 20 so that the protrusion 24 of the mating ferrule fits into the irregularity 33 in the slot 31 of the proximal ferrule. Any desired knot, such as a square knot or a Roeder knot, is formed in the knot material 50 and a free end of the knot material 50 is terminated with a needle 52. The knot material 50 is wound around the mating ferrule 20 and the proximal ferrule 30, with the needle 52 and an amount of knot material 50 hanging free off of the mating ferrule 20 and the remaining free end of the knot material 50 terminated in the annular notch 37 in the proximal ferrule 30. The termination in the notch 37 may be a cinch knot.

The knot material 50 is wound with sufficient tension so that the windings will remain stationary with respect to each other and the cartridge before the knot deployment process is initiated, but not so tight as to prevent the knot material 50 from sliding along the mating ferrule 20 when the knot deployment process is initiated. The cartridge is completed by placing the thread cover 40 over the proximal ferrule 30 so that the protrusion 34 of the proximal ferrule 30 fits through the slot 51 of the thread cover 40.

The thread cover 40 prevents the knot material 50 from losing too much tension. If the windings start to detach from the mating ferrule 20, they will come into contact with the thread cover 40 before they can further unwind.

In a preferred embodiment, the knot carrier tube 10 is manufactured of metal. Unlike the knot carrying cartridge, the knot carrier tube 10 is designed to be used repeatedly. As previously described, the cartridge is installed for use on the knot carrier tube 10 by screwing the mating ferrule 20 onto the appropriate end of the knot carrier tube 10. After the cartridge is used to tie a knot, the cartridge is simply unscrewed and a new cartridge may be installed when needed.

It should be appreciated that other embodiments of the invention may produce substantially the same results by the same methods as has been hereinabove described. As an example, the knot carrier tube and the mating ferrule could be combined as one piece having the same shape as the connected mating ferrule 20 and knot carrier tube 10. This would be particularly useful to produce a completely disposable knot placing device and is an alternate design. As another example, the proximal ferrule 30 and the thread cover could be combined as one piece, although this may complicate the manufacturing process.

What is claimed is:

1. A thread cover for a knot tying apparatus, said knot tying apparatus being used for placing an at least partially formed knot located between a first end and a second end of a thread, comprising:
   (a) a sheath surrounding an inner cavity, said sheath having a proximal end, and a distal end, said inner cavity being sized and shaped to accommodate a thread disposed therein, and wherein said sheath is adapted at said proximal end to be connected to a knot slider, said knot slider acting to displace at least a portion of said thread into said cavity; and
   (b) a notch in said distal end of said sheath, wherein the width of said notch is sufficient to allow said thread to slide therethrough while preventing said at least partially formed knot in said thread from sliding therethrough, thereby allowing said at least partially formed knot to be pushed by said thread cover along a portion of said thread.

2. A thread cover according to claim 1, wherein said sheath contains an aperture near said proximal end, and wherein said knot slider includes a protrusion which fits into said aperture.

3. A thread cover according to claim 1, wherein said sheath includes a plurality of notches at said distal end.

4. A thread cover according to claim 3, wherein said sheath includes two notches.

5. A thread cover according to claim 1, wherein said sheath is substantially cylindrical.

6. A thread cover according to claim 5, wherein said sheath includes two notches which are spaced approximately 180 degrees apart.

7. A knot tying apparatus for use in placing a knot near a member, comprising:
   (a) a knot carrier;
   (b) a knot slider slidably attached to said knot carrier;
   (c) a thread having a first end and a second end and an at least partially formed knot located therebetween, a portion of said thread being initially wound around said knot carrier and said first end of said thread being attached to said knot slider; and
   (d) a thread cover having a proximal end and a distal end, said thread cover proximal end connected to said knot slider distal end, and said thread cover at least partially surrounding said knot carrier and including a notch in said distal end, wherein the width of said notch is sufficiently wide to allow said thread to slide therethrough while preventing said at least partially formed knot from sliding therethrough, thereby allowing said at least partially formed knot to be pushed along said thread by said thread cover.

8. A knot tying apparatus according to claim 7, further including a needle, said needle being attached to said second end of said thread.

9. A knot tying apparatus according to claim 8, further including a jaws for pulling on said needle or said second end of said thread, said jaws capable of being retracted so as to be at least partially surrounded by said thread cover.

10. A knot tying apparatus according to claim 8, wherein said at least partially formed knot is initially located on said knot carrier at a point distal from said knot slider, whereby sliding said knot slider distally pushes said at least partially formed knot distal to said knot carrier.

11. A knot tying apparatus according to claim 7, wherein said thread cover includes a plurality of notches at said distal end.

12. A knot tying apparatus according to claim 11, wherein said thread cover includes 2 notches.

13. A knot tying apparatus according to claim 7, wherein said thread cover is a substantially cylindrical sheath.

14. A knot tying apparatus according to claim 13, wherein said thread cover includes 2 notches at said distal end, said 2 notches being spaced approximately 180 degrees apart.

15. A knot tying apparatus according to claim 7, wherein said thread cover includes an aperture at said proximal end of said thread cover, and wherein the distal end of said knot slider includes a protrusion which fits into said aperture.

16. A knot tying apparatus for use in placing a knot near a member, comprising:
   (a) a knot carrier having a proximal end and a distal end;
   (b) a knot slider slidably attached to said knot carrier;
   (c) a thread having a first end and a second end and an at least partially formed knot located therebetween, said at least partially formed knot initially located on said knot carrier distal to said knot slider, and wherein said knot slider is a sheath that is attached to said knot carrier at a position proximal to said at least partially formed knot, and wherein said first end of said thread is attached to said knot slider; and
   (d) a thread cover having a proximal end and a distal end, said thread cover proximal end being attached to said knot slider, said thread cover at least partially surrounding said knot carrier and being spaced away from said knot carrier sufficiently such that said at least partially formed knot initially resides between said knot carrier and said thread cover, and said thread cover distal end including a notch, wherein the width of said notch is sufficiently wide to allow said thread to slide therethrough while preventing said at least partially formed knot from sliding therethrough, thereby allowing said at least partially formed knot to be pushed along said thread by said thread cover.

17. A knot tying apparatus according to claim 16, wherein said knot slider snugly fits around said knot carrier at a position proximal to said at least partially formed knot, and wherein said thread cover is attached to said knot slider proximal to first end of said thread and extends distally beyond said knot carrier.

18. A knot tying apparatus according to claim 16, further including:
(a) an elongate tube having a proximal end and a distal end, said elongate tube distal end being connected to said knot carrier; and
(b) an actuating tube having a first end and a second end which overlaps said elongate tube, said actuating tube first end abutting said knot pusher proximal end, and said actuating tube second end being located between said knot slider and said elongate tube proximal end.

19. A method of placing and tying a knot using a knot tying apparatus, comprising:
(a) positioning said knot tying apparatus adjacent a member to which an at least partially formed knot is to be applied, said knot tying apparatus including a knot slider and a thread cover, each having a proximal end and a distal end, said thread cover proximal end being connected to said knot slider distal end, and said thread cover distal end having a notch for engaging an at least partially formed knot located between a first and second end of a thread, said notch being sufficiently wide to allow said thread to slide therethrough while preventing said at least partially formed knot in said thread from sliding therethrough;
(b) placing said at least partially formed knot adjacent said member using said knot tying apparatus;
(c) engaging said at least partially formed knot with said notch in said thread cover; and
(d) sliding said at least partially formed knot along a portion of said thread with said thread cover in a first direction.

20. A method according to claim 19, wherein said knot tying apparatus further including a knot carrier, said knot carrier having a proximal end and a distal end, said knot slider being slidably attached to said knot carrier, said knot carrier being at least partially surrounded by said thread cover, and said at least partially formed knot initially being located on said knot carrier.

21. A method according to claim 20, wherein said first end of said thread is attached to said knot slider and said at least partially formed knot is located distal to said knot slider, and wherein said placing step includes sliding said knot slider distally, thereby pushing said at least partially formed knot distal to said knot carrier.

22. A method according to claim 19, wherein said engaging step involves placing said at least partially formed knot in abutting relationship with the exterior of said thread cover and said notch.

23. A method according to claim 19, further including a pulling step, wherein said pulling step involves pulling on said knot tying apparatus in a second direction.

24. A method according to claim 23, wherein said first direction is toward said member and wherein said second direction is away from said member.

25. A method according to claim 23, said knot tying apparatus further including a needle, said needle being attached to said thread second end, and wherein said pulling step includes pulling on said needle.

26. A method according to claim 25, said knot tying apparatus further including a pair of jaws, said jaws being capable of being retracted so as to be at least partially surrounded by said thread cover, and wherein said pulling step involves pulling on said needle with said jaws.

27. A method according to claim 23, wherein said sliding step and said pulling step are performed simultaneously to minimize pulling forces on said member.

28. A method according to claim 26, wherein said sliding step and said pulling step are performed simultaneously to minimize pulling forces on said member.

29. A method for placing and tying a knot using a knot tying apparatus, comprising:
(a) positioning said knot tying apparatus adjacent a member to which an at least partially formed knot is to be applied, said knot tying apparatus including (I) a knot carrier having a proximal end and a distal end, (ii) a knot slider slidably attached to said knot carrier, (iii) a thread having a first end and a second end and an at least partially formed knot located therebetween, said at least partially formed knot initially located on said knot carrier distal to said knot slider, and wherein said knot slider is a sheath that is attached to said knot carrier at a position proximal to said at least partially formed knot, and wherein said first end of said thread is attached to said knot slider, and (iv) a thread cover having a proximal end and a distal end, said thread cover proximal end being attached to said knot slider, said thread cover at least partially surrounding said knot carrier and being spaced away from said knot carrier sufficiently such that said at least partially formed knot initially resides between said knot carrier and said thread cover, and said thread cover distal end including a notch, wherein the width of said notch is sufficiently wide to allow said thread to slide therethrough while preventing said at least partially formed knot from sliding therethrough, thereby allowing said at least partially formed knot to be pushed along said thread by said thread cover;
(b) placing said at least partially formed knot adjacent said member using said knot tying apparatus;
(c) engaging said at least partially formed knot with said notch in said thread cover; and
(d) sliding said at least partially formed knot along a portion of said thread with said thread cover in a first direction.

30. A method according to claim 29, wherein said placing step includes sliding said knot slider distally, thereby pushing said at least partially formed knot distal to said knot carrier.

31. A method according to claim 29, further including a pulling step, wherein said pulling step involves pulling on said knot tying apparatus in a second direction.

32. A method according to claim 31, wherein said first direction is toward said member and wherein said second direction is away from said member.

33. A method according to claim 31, said knot tying apparatus further including a needle attached to said thread second end, and wherein said pulling step includes pulling on said needle.

34. A method according to claim 33, said knot tying apparatus further including a pair of jaws, said jaws being capable of being retracted so as to be at least partially surrounded by said thread cover, and wherein said pulling step involves pulling on said needle with said jaws.

35. A method according to claim 31, wherein said sliding step and said pulling step are performed simultaneously to minimize pulling forces on said member.

36. A method according to claim 34, wherein said sliding step and said pulling step are performed simultaneously to minimize pulling forces on said member.

* * * * *